(12) United States Patent
Bodenschatz et al.

(10) Patent No.: US 7,052,478 B1
(45) Date of Patent: May 30, 2006

(54) BANDAGE FOR THE ARM WITH ENCLOSURE FOR THE SHOULDER

(75) Inventors: Stefan Bodenschatz, Buxtehude (DE); Thorsten Herzberg, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/445,065

(22) PCT Filed: May 28, 1998

(86) PCT No.: PCT/EP98/03160

§ 371 (c)(1), (2), (4) Date: Dec. 1, 1999

(87) PCT Pub. No.: WO98/56322

PCT Pub. Date: Dec. 17, 1998

(30) Foreign Application Priority Data

Jun. 10, 1997 (DE) ............................... 197 24 322

(51) Int. Cl.
*A61F 5/00* (2006.01)
*A61F 5/37* (2006.01)

(52) U.S. Cl. .............................. 602/5; 602/20; 128/878
(58) Field of Classification Search ............... 602/4–8, 602/20–21, 60–63; 128/878–879, DIG. 19
See application file for complete search history.

(56) References Cited

U.S. PATENT DOCUMENTS

| | | | |
|---|---|---|---|
| 4,214,579 A * | 7/1980 | Ford | 128/94 |
| 4,446,858 A * | 5/1984 | Verter | 602/4 |
| 4,550,869 A * | 11/1985 | Johnson | 224/202 |
| 4,753,240 A | 6/1988 | Sparks | |
| 4,759,353 A * | 7/1988 | Melendez | 128/94 |
| 5,383,844 A * | 1/1995 | Munoz et al. | 602/20 |
| 5,405,312 A | 4/1995 | Jacobs | |
| 5,415,623 A * | 5/1995 | Cherubini | 602/7 |
| 5,599,283 A * | 2/1997 | Lindenmeyer et al. | 602/5 |
| 6,099,489 A * | 8/2000 | Herzberg et al. | 602/4 |
| 6,152,891 A * | 11/2000 | Carlson | 602/4 X |

FOREIGN PATENT DOCUMENTS

| | | |
|---|---|---|
| DE | 36 12 426 | 10/1987 |
| EP | 0 198 482 | 10/1986 |
| EP | 0 589 663 | 3/1994 |
| SU | 32/252 A * | 11/1971 ............ 602/4 |

OTHER PUBLICATIONS

English-language abstract of German patent No. 3612426 dated Oct. 22, 1987.
English-language abstract of European patent No. 0198482 dated Oct. 22, 1986.

* cited by examiner

*Primary Examiner*—Michael A. Brown
*Assistant Examiner*—Fenn C. Mathew
(74) *Attorney, Agent, or Firm*—Alston & Bird LLP

(57) ABSTRACT

Bandage for the shoulder and upper arm area, comprising an anatomically shaped upper arm part which receives the upper arm, and an anatomically shaped forearm part which receives the forearm, the upper arm part being designed in the shape of a half shell and having a cap-like recess for receiving the shoulder joint, and the forearm part being designed in the shape of a half shell and having an enclosure for the elbow joint, the upper arm part and the forearm part being connected to one another in an adjustable manner, and a support strap being arranged on the upper arm part and a holding strap being arranged on the forearm part.

19 Claims, 2 Drawing Sheets

BANDAGE FOR THE ARM WITH ENCLOSURE FOR THE SHOULDER

The invention relates to a bandage for the arm with an enclosure for the shoulder and, if appropriate, an integrated hand guide.

BACKGROUND OF THE INVENTION

Depending on their design and on the indications for which they are intended, orthopaedic bandages exert a fixing, guiding, bracing and/or supporting action on the extremities of the human body.

These medical bandages must have a three-dimensional shape which corresponds to the anatomical circumstances in order to be able to act externally on the human body with a form fit and a force fit.

Medical bandages of this kind are produced by cutting out blanks from planar material, for example neoprene, knitted fabrics or woven fabrics. The anatomically appropriate shape is obtained via the shape of the blanks or darts, for example with gussets, and subsequent joining together of the blanks, as is also customary in articles of clothing.

The joining together can be done by sewing, gluing or other conventional methods. The great disadvantage of these bandages is that the exact anatomical fit can be achieved only with difficulty and there are a large number of connection points, for example seams. These connection points change the properties of the material used, and there is the danger of pressure points on the skin.

This risk occurs most often in the case of compression stockings and bandages for burns. The bandages for burns usually have a large number of seams, for example in the region of the female breast and in the facial region, and these often lead to pressure points.

Another possible way of producing medical bandages is shaped knitting with flat knitting machines or circular knitting machines. However, this method is limited in terms of the possibility of shaping and the choice of material. In particular, only two-dimensional shaping is possible. The third dimension can only be achieved by subsequent sewing, in other words with rather undesirable seams. The production is complicated.

Bandages are also known in which foam rubber is deformed under compression moulding to different thicknesses. In this way, as a result of the different density of the foam after deformation, the elastic properties of the material can be locally altered. Such a bandage is described, for example, in WO 95/32690.

A correct fit to the anatomical shape is not achieved in this way.

It is moreover known to shape thermoplastic plate material anatomically correctly to give orthopaedic ortheses and prostheses of suitable form. These materials, for example polyethylene (HDPE), polypropylene or a PP copolymer, have a thermoplastic deformation range of about 170° C. to 250° C. and are substantially rigid after cooling, so that they cannot be used for medical bandages.

DE-P-43 14 785 discloses a bandage system particularly intended for acromioclavicular luxations and lateral fractures of the clavicle. The bandage system is made up of a tube part which receives the forearm and upper arm and which is made of a fabric which is radially elastic but which is essentially non-stretchable in the longitudinal direction, a support band, a holding band, closure members which are provided on the said bands for forming holding loops, and a tightening strap. Such a bandage is suitable for achieving a diminution of the presented indications, but it is very complicated to produce. Moreover, because of the tubular construction, it is often difficult for the patient to fit the bandage without pain.

The object of the invention was therefore to make available a bandage which, by means of an explicit shape fit, ensures secure and stable fixation of the shoulder and of the upper arm and does not have the cited disadvantages of the prior art.

SUMMARY OF THE INVENTION

Accordingly, the bandage for the shoulder and upper arm region comprises an anatomically shaped upper arm part which receives the upper arm, and an anatomically shaped forearm part which receives the forearm, the upper arm part being designed in the shape of a half shell and having a cap-like recess for receiving the shoulder joint, and the forearm part being designed in the shape of a half shell and having an enclosure for the elbow joint.

In addition, the upper arm part and the forearm part are connected to one another in an adjustable manner. Finally, a support strap is arranged on the upper arm part and a holding strap is arranged on the forearm part in order to fix the bandage according to the invention on the body.

The starting material for producing the upper arm part and the forearm part is preferably a thermoformable nonwoven fabric, a thermoformable foam and/or a thermoformable plastic with low rigidity, the starting material comprising at least 10% by weight of thermoformable material.

Such starting materials are distinguished by the fact that on the one hand they are soft, and yet, on the other hand, they have sufficient shape stability and a low weight.

The upper arm part and the forearm part are advantageously surrounded by an encapsulating material.

In addition, the edges of the upper arm part and/or of the forearm part are preferably thin or conical. These edges can be produced by welding or sewing.

In a preferred embodiment, profiled recesses are worked into the upper arm part and/or the forearm part and exert a partial strengthening action.

In a further advantageous embodiment, the forearm part has a hand guide or hand-securing means.

If appropriate, the hand guide can be individually shortened, depending on the therapy and the indication, in order to ensure an optimum fit.

The upper arm part is preferably fixed ventrally to the forearm in the area of the wrist by means of a support strap which runs from the shoulder to the neck area, and the support strap can comprise a partial padding in the area of transition from the cervical spine to the shoulder girdle. The partial padding has the function of distributing the occurring loads evenly over the surface. In addition, the support strap is designed partially divided in two parts, preferably immediately after the attachment point on the shoulder cap, so as to be able to be fixed both ventrally and also dorsally on the thorax.

The holding strap advantageously runs from the forearm part, starting from the hand region, dorsally in the lumbar area to the distal upper arm and laterally encloses the latter from posterior to anterior.

The straps can be fixed, for example, using VELCRO® hook and loop closures or press studs.

The straps, that is to say the support strap and the holding strap, are preferably made of a laminated foam or a laminated nonwoven fabric.

Finally, it has proven particularly advantageous if the straps have a high padding effect and, with loading of about 50 N, have a preferred longitudinal expansion of <35%, particularly preferably a longitudinal expansion of <10%.

The upper arm part and the forearm part are preferably connected to one another in an adjustable manner.

The upper arm part and the forearm part can in this case be connected to one another by means of a VELCRO® hook and loop closure, press studs or seams. An adjustable connection is provided in particular to meet the individual lengths of the extremities and thereby to improve the shape fit efficiency.

The bandage according to the invention serves in particular as a post-traumatic and post-operative special bandage for injuries in the shoulder and upper arm area, for example distorsions, rotator injuries, periarthritis humeroscapularis, luxations of the shoulder joint, fractures of the shoulder blade and subcapitular fractures of the humerus, fractures of the head of the upper arm and fractures of the shaft of the upper arm.

A special bandage of this kind must have the characteristics according to the invention in order to be able to act correctly for the indication:

an explicit shape fit in order to ensure a secure and stable fixation of the shoulder and of the upper arm,
a well enclosed shoulder joint with corresponding fixation transition to the thoracic area.

Depending on indication, fixation of the forearm with an integrated hand guide is also necessary in order to substantially guarantee success of treatment. In the same way as with conventional plaster cast therapy, one or two joints of an affected joint are always bridged in order to ensure effective therapy.

The fixation of the forearm also provides additional relief of the shoulder joint, which has a positive effect on the muscles and ligaments and rules out irritation of the nerve structures involved.

The straps can be fixed, for example, using VELCRO® hook and loop closures or press studs.

These criteria are satisfied by using two three-dimensionally shaped moulded parts, namely an upper arm part and a lower arm part, which correspond to the anatomical circumstances of the arm and of the shoulder.

The open, half-shell structure also permits straightforward and painless application of the bandage according to the invention. This is a particular advantage, especially as the patient can apply the bandage himself.

The upper arm part and the forearm part can in this case be connected to one another by means of a VELCRO® hook and loop closure, press studs or seams. An adjustable connection is provided in particular to meet the individual lengths of the extremities and thereby to improve the shape fit efficiently.

The upper arm part and the forearm part, hereinafter referred to simply as shaped parts, for producing the bandage according to the invention are obtained by three-dimensional adaptation of a starting material, which contains at least a proportion of thermoplastic fibres or components, preferably to at least 10% by weight, to the shape of the body part on which they are to be used.

The starting material is preferably a thermoformable nonwoven fabric, a thermoformable foam and/or a thermoformable plastic of low rigidity. Possible plastics having such low rigidity are polyethylene (LDPE), polypropylene and mixtures of the said polymers. In addition, these starting materials can be mixed with other copolymers.

The starting material is also preferably a thermoformable woven fabric or knitted fabric in which elastic fibres or components can be incorporated. The use of a thermoformable foil is also possible.

The materials listed can be made elastic by incorporation of, for example, elastane or elstodiene.

The starting material is also preferably connected to form two-layer or multi-layer laminates, of which at least one layer is thermoformable, and the lamination is carried out using generally known methods, for example lining.

A shaped part can advantageously be produced by starting material, which has been cut to the appropriate shape fit, being heated to the thermoplastic softening point, and this starting material then being pressed to the required shape by means of a positive mould and/or negative mould which is designed corresponding to the anatomical circumstances of the particular body part.

The shaped part is also advantageously produced by the starting material, which has been cut to the appropriate shape fit, being heated to the thermoplastic softening point and pressed to the required shape between a positive mould and a negative mould, which are designed corresponding to the anatomical circumstances of the particular body part.

The heating can be carried out using heatable moulds, or by means of the starting material first being suitably heated in an oven and only then shaped in the moulds.

To individually configure the shaped parts, it is necessary to determine the anatomical measurements of the relevant body parts of the patient concerned. This can be done using a computer-aided measurement method, for example scanning, or by simple manual measurement. In addition, an impression of the body part can be taken with wax or plaster. The latter in particular facilitates the production of correspondingly designed positive and negative moulds.

If shaped parts are needed in very large batch numbers, generally conventional anatomical measures can be used to produce the necessary shapes.

The shaped parts according to the invention can be produced easily and inexpensively because they do not have to be joined together or shape-knitted from a large number of blanks in order to achieve the required shape fit.

A particularly advantageous embodiment of the bandage according to the invention is described below with reference to a number of figures, without thereby unnecessarily restricting the invention.

Figure 1:
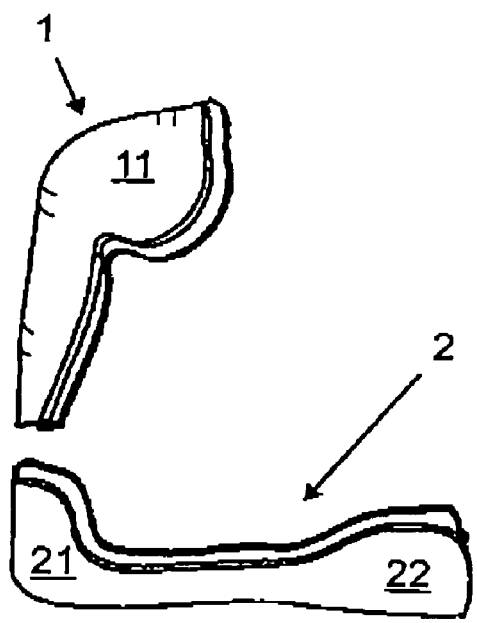
FIG. 1 shows the upper arm part and the forearm part in a side view.

In FIG. 1, the upper arm part 1 and the forearm part 2 are represented in a side view.

The upper arm part 1 is in this case designed as a half shell in such a way that it provides an excellent fit to the anatomical circumstances of the right upper arm and the right shoulder of the patient, since the cap-shaped recess 11 is able easily to receive the shoulder joint. The shoulder is here enclosed at the same time as the upper arm in a half shell.

The forearm part 2 is likewise designed as a half shell and adapted to the anatomical circumstances of the right forearm, so that it can perfectly receive or enclose the right elbow joint of the patient within the recess 21. In the area of the hand, the forearm part 2 has a hand part 22 which serves for fixing the hand and at the same time for supporting the wrist. The fingers are also guided in the hand part 22.

Figure 2:
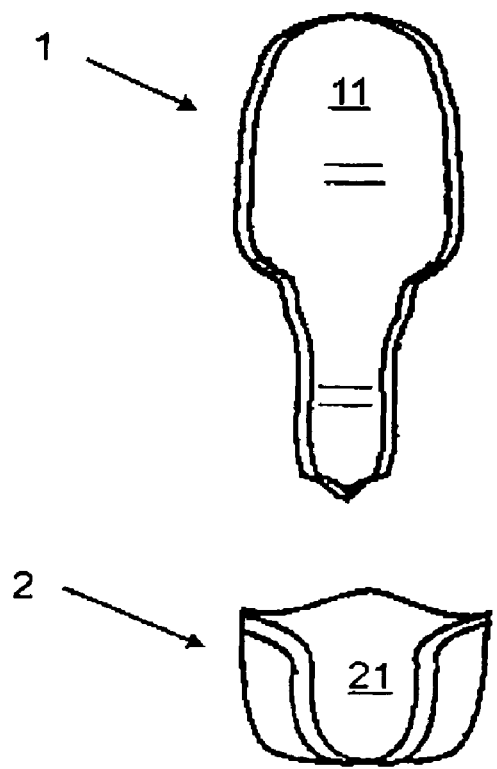
FIG. 2 shows the upper arm part and the forearm part from the front.

In FIG. 2, the upper arm part 1 and the forearm part 2 are represented as viewed into the recesses 11 and 21, respectively. The width of the upper arm part 1 is adapted to the measurements of the shoulder of the patient so that the upper arm part 1 sits firmly on the shoulder, but without exerting pressure. The same applies to the forearm part 2. The diameter of the forearm part 2 is chosen according to the measurements of the wrist, then widens in the area of the forearm musculature and finally narrows again so that the elbow joint is supported in the area of the recess.

Figure 3:
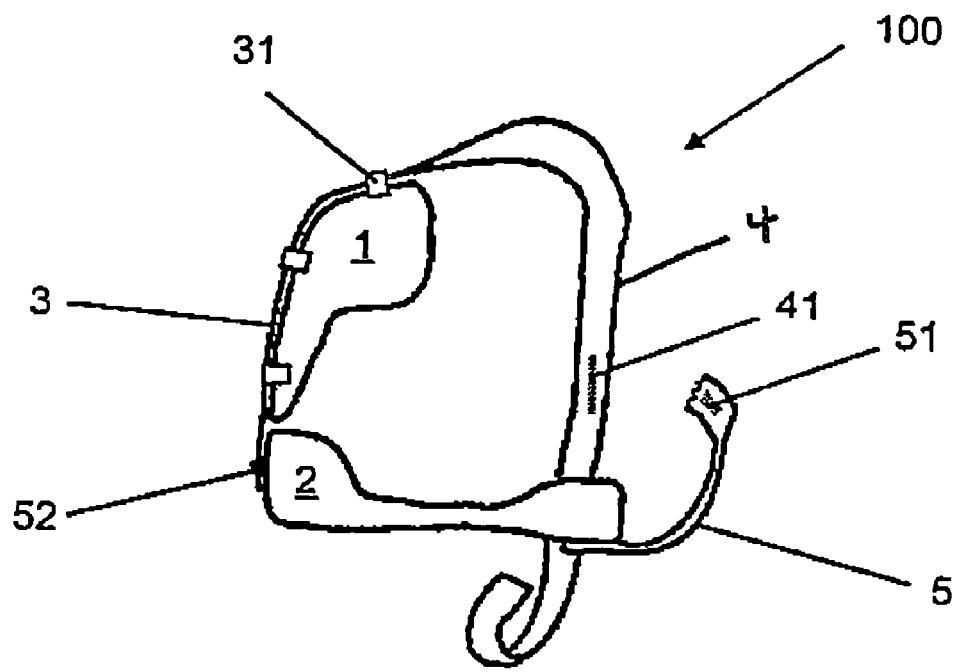
FIG. 3 shows the bandage, comprising upper arm part and forearm part and connection arrangements and straps.

The bandage 100 shown in FIG. 3 is made up essentially of the upper arm part 1 and the forearm part 2, which are connected to one another in a substantially flexible manner via an appropriately shaped connection strap 3. The connection strap 3 is secured on the upper arm part 1 by means of VELCRO® hook and loop closures, and the connection to the forearm part 1 is effected by a press stud 52. The securing by VELCRO® hook and loop closures 31 ensures that the bandage can be adapted to the individual circumstances of the patient's arm.

The upper arm part 1 is fixed ventrally to the forearm in the area of the wrist by a support strap 4 which runs from the shoulder to the neck area. The support strap 4 is fixed by means of a VELCRO® hook and loop closure 41. The forearm part 2 is fixed with a holding strap 5 which, starting from the hand region, runs dorsally in the lumbar area to the distal upper arm. The holding strap 5 is secured by a VELCRO® hook and loop closure 51. The whole strap system together secures the position of the bandage on the patient.

Figure 4:
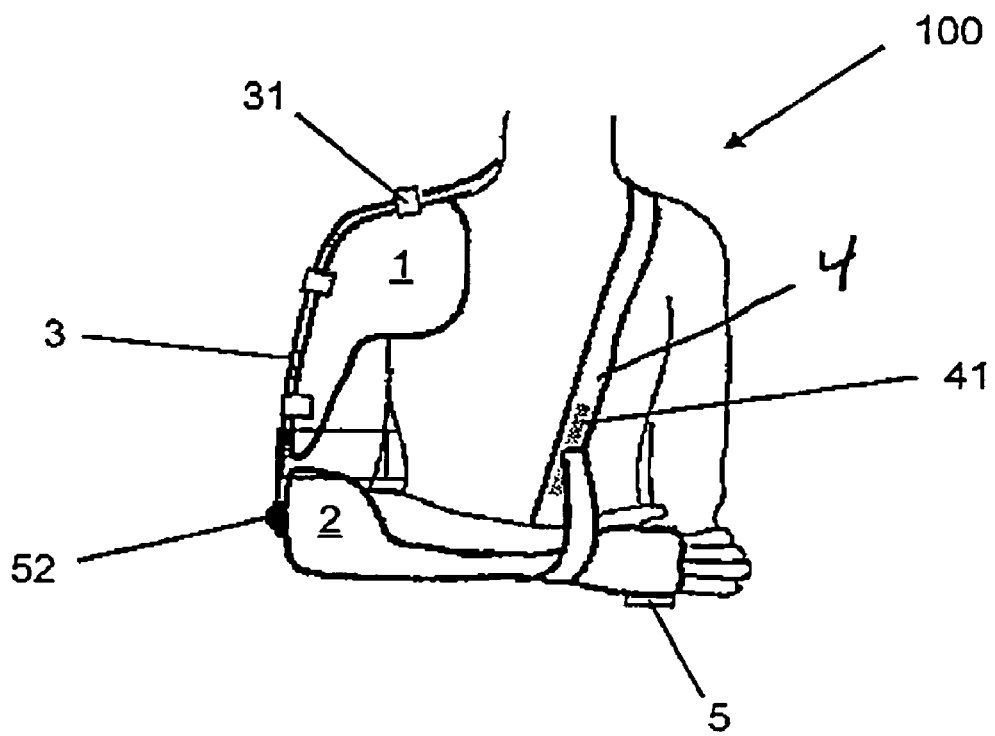
FIG. 4 shows the bandage according to the invention applied on a patient.

Finally, FIG. 4 shows how the bandage 100 according to the invention is applied on the right shoulder and right forearm of the patient. Starting from the patient's wrist, the holding strap 5 runs behind his back and is guided round the right upper arm in a loop and fixed to the holding strap 5 itself, namely by means of the VELCRO® hook and loop closure 51, behind the patient's back.

The invention claimed is:

1. Bandage for the shoulder and upper arm area, comprising an anatomically shaped upper arm part which is configured to receive the upper arm of a patient, and an anatomically shaped forearm part which is configured to receive the forearm of said patient,
   the upper arm part being designed in the shape of a half shell and having a recess configured to fit over and enclose the shoulder joint of said patient in said half shell, and
   the forearm part being designed in the shape of a half shell and having an enclosure for the elbow joint configured to extend along the forearm of the patient, and
   the upper arm part and the forearm part being connected to one another by a connecting strap in an adjustable and substantially flexible manner, and a support strap being arranged on the upper arm part and a holding strap being arranged on the forearm part wherein at least a portion of the holding strap is configured to extend generally parallel to the forearm of the patient and the forearm part, said holding strap being configured to pass laterally behind and across the back of a patient to the upper arm part and form a loop around the upper arm part and the upper arm of the patient below a shoulder of the patient, one end of said holding strap being fixed to the forearm part and the second end of said holding strap being secured to the upper arm part, thereby holding the forearm part against the body of said patient.

2. Bandage according to claim 1, wherein the upper arm part and the forearm part are surrounded by an encapsulating material.

3. Bandage according to claim 1, wherein the edges of the upper arm part, forearm or both are thin or conically shaped.

4. Bandage according to claim 1, wherein, in addition to the recess adapted to fit over and enclose the shoulder, the upper arm part comprises profiled recesses which exert a partial strengthening action.

5. Bandage according to claim 1, wherein profiled recesses can be worked into the forearm part and exert a partial strengthening action.

6. Bandage according to claim 1, wherein the forearm part has a hand guide or hand-securing means.

7. Bandage according to claim 1, wherein the upper arm part is fixed ventrally to the forearm part in the area of the wrist by means of said support strap and said support strap runs from the shoulder to the neck area.

8. Bandage according to claim 1, wherein the support strap comprises a partial padding in the area of transition from the cervical spine to the shoulder girdle.

9. Bandage according to claim 1 wherein the holding strap runs from the forearm part, starting from the hand region, dorsally in the lumbar area to the distal upper arm and laterally encloses the latter from posterior to anterior.

10. Bandage according to claim 1, wherein the straps are made of a laminated foam or a laminated nonwoven fabric.

11. Bandage according to claim 1, wherein the straps have a high padding effect and, with loading of about 50 N, have a longitudinal expansion of <35%.

12. Method of producing a bandage according to claim 1 wherein the upper arm part and the forearm part are made of a starting material which contains at least a proportion of thermoplastic fibres or components, and are thermoformed to the shape of the body part on which they are to be used.

13. Method according to claim 12, wherein said starting material is a thermoformable nonwoven fabric, woven fabric, knitted fabric, foil, foam, thermoformable plastic with low rigidity or a combination thereof.

14. Method according to claim 12, wherein the starting material comprises a two-layer or multi-layer laminate, of which at least one layer is thermoformable.

15. Method according to claim 12, wherein the starting material is heated to thermoformability and is then shaped using a positive mould, negative mould or both.

16. Method according to claim 12, wherein the starting material is heated to its thermoformability point and is shaped between a positive mould and a negative mould.

17. Method according to claim 12, wherein the starting material is heated to its thermofomability point and formed in heated moulds.

18. Method according to claim 12, wherein the starting material has been thermoformed to individual body sizes.

19. Bandage according to claim 11, wherein said longitudinal expansion is <10%.

* * * * *